United States Patent [19]
Bouboulis

[11] 3,950,310

[45] Apr. 13, 1976

[54] POLYAMIDES FROM CYCLOHEXANE BIS(ETHYLAMINE)

[75] Inventor: Constantine J. Bouboulis, Union, N.J.

[73] Assignee: Exxon Research & Engineering Co., Linden, N.J.

[22] Filed: Feb. 23, 1972

[21] Appl. No.: 228,622

Related U.S. Application Data

[63] Continuation-in-part of Ser. No. 115,140, Feb. 12, 1971, abandoned, which is a continuation of Ser. No. 718,934, April 4, 1968, abandoned.

[52] U.S. Cl. ....... 260/78 R; 260/33.4 R; 260/47 CZ; 260/563 C
[51] Int. Cl.² ......................................... C08G 69/26
[58] Field of Search .................................. 260/78 R

[56] References Cited
UNITED STATES PATENTS

| | | | |
|---|---|---|---|
| 2,324,936 | 7/1943 | Kroeper et al. | 260/78 R |
| 2,577,621 | 12/1951 | May et al. | 260/78 R |
| 3,012,994 | 12/1961 | Bell et al. | 260/78 R |

FOREIGN PATENTS OR APPLICATIONS

| | | | |
|---|---|---|---|
| 924,240 | 2/1955 | Germany | 260/78 |

*Primary Examiner*—Harold D. Anderson
*Attorney, Agent, or Firm*—Anthony A. Lagani, Jr.; William T. Clarke

[57] ABSTRACT

Novel polyamides are prepared by reacting a dicarboxylic acid with 1,4-cyclohexane-bis($\beta$-ethylamine). Unique properties are obtained where the dicarboxylic acid is 1,4-cyclohexane diacetic acid. The polymers of this invention are distinguished from the prior art in that they exhibit unexpectedly high melting points and crystallinity. Thence they are suitable for use in fibers as well as molding and other general polyamide applications.

4 Claims, 1 Drawing Figure

DIFFERENTIAL THERMAL ANALYSIS OF ANALOGOUS POLYAMIDES
Figure IA
DTA OF CYCLOHEXANE bis(METHYLAMINE)/ADIPIC ACID POLYAMIDE
(70% cis/30% trans)
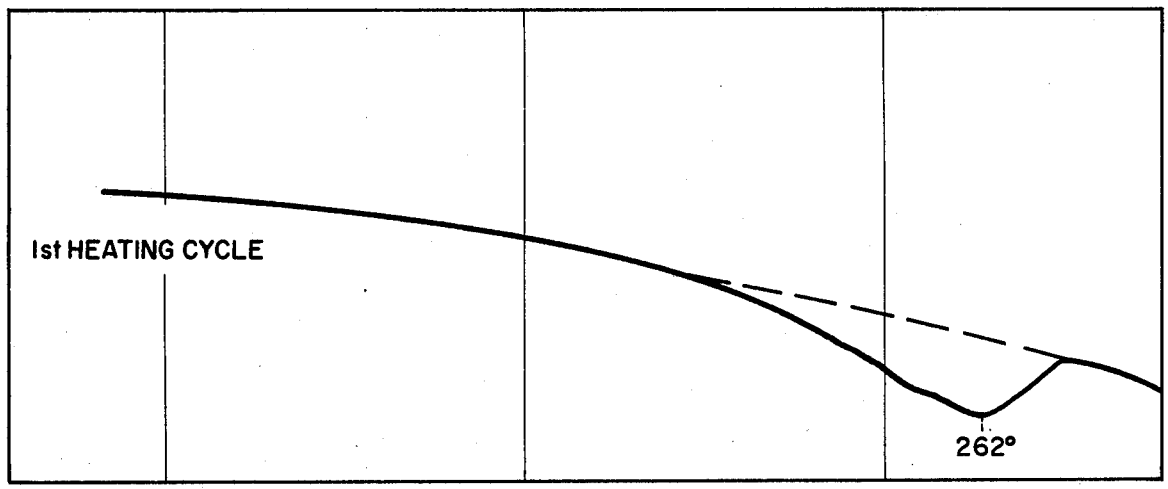
Figure IB
DTA OF CYCLOHEXANE bis(ETHYLAMINE)/ADIPIC ACID POLYAMIDE
(70% cis/30% trans)
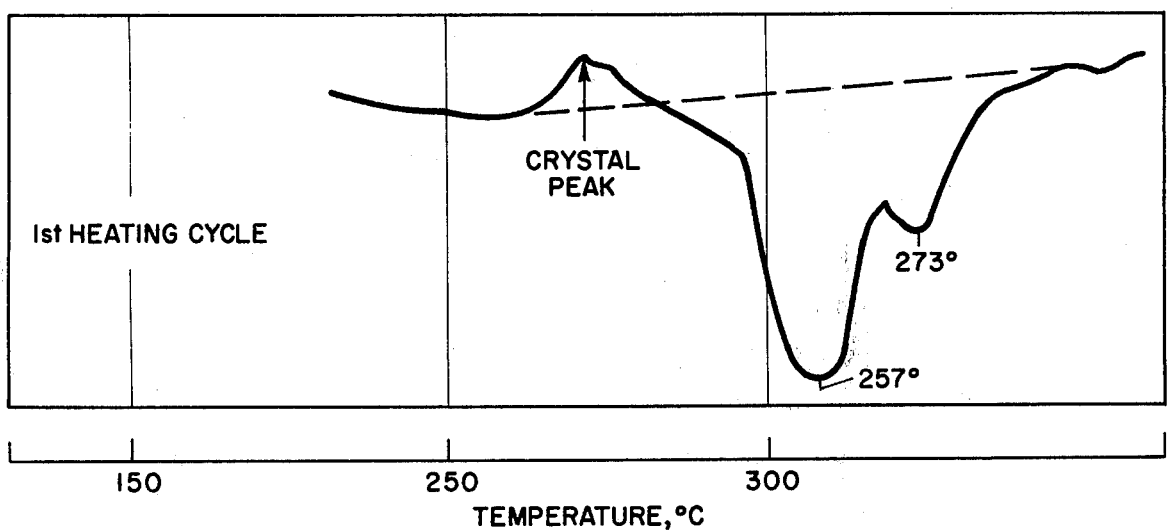

POLYAMIDES FROM CYCLOHEXANE BIS(ETHYLAMINE)

CROSS-REFERENCE TO RELATED APPLICATIONS

This application is a continuation-in-part of U.S. application Ser. No. 115,140, filed Feb. 12, 1971, now abandoned, which in turn is a streamline continuation of Ser. No. 718,934, filed Apr. 4, 1968 now abandoned.

BACKGROUND OF INVENTION

It is well known to prepare polyamides of bifunctional carboxy compounds and diamines. Polyamides are advantageously employed in the manufacture of fibers, yarns, fabrics, film, extruded products, coating compositions, electrical insulations, molding compositions, etc.

For a number of years a polyamide, commonly known as Nylon 66, derived from the condensation of adipic acid and hexamethylene diamine has enjoyed commercial success because of its excellent properties. Nylon 6, a closely related polyamide is derived from the self-condensation of epsilon-caprolactam. 1,4-cyclohexane-bis(methylamine) has been incorporated in nylon 6-type polyamides as a modifier; see, for example, U.S. Pat. No. 2,985,627, incorporated herein by reference.

High melting polyamides have been prepared from essentially trans 1,4-cyclohexane-bis(methylamine). As the percentage of cis isomer increases, the melting point decreases; see, for example, U.S. Pat. No. 3,012,994, incorporated herein by reference.

It is well known that as the lengths of the diamine molecule increases, the melting point of the polymer decreases. Available prior art data would lead to the prediction that for a given diacid an increase in the length of the diamine chain by two methylene groups should result in about a 20°C. *decrease* in melting point of the resulting polyamide.

SUMMARY OF THE INVENTION

It has now been found that polyamides formed from 1,4-cyclohexane-bis($\beta$-ethylamine) have melting points about 10°C. *above* the analogous polyamides formed from 1,4-cyclohexane bis(methylamine) [CBM], a homologue of 1,4-cyclohexane-bis($\beta$-ethylamine) [CBE] containing two less methylene groups. Furthermore, the polyamides of this invention have improved properties over CBM polyamides or nylon 6,6.

It has been found that CBE/adipic acid (CBE-6) polyamide has higher crystallinity and lower moisture absorption than the anologous CBM-6 polyamide. Additionally, it has a higher elastic modulus and elongation than nylon 6,6. In general, CBE-6 polyamide combines the best properties of both CBM-6 and nylon 6,6 polyamides. Its excellent dimensional stability makes it especially well suited for molded articles in addition to tire cord, fibers, etc.

BRIEF DESCRIPTION OF THE DRAWINGS

FIG. 1A shows the differential thermal analysis curve for cyclohexane bis(methylamine)/adipic acid polyamide.

FIG. 1B shows the differential thermal analysis curve for cyclohexane bis(ethylamine)/adipic acid polyamide.

DETAILED DESCRIPTION

This invention relates to a novel polyamide derived from a dicarboxylic acid and 1,4-cyclohexane-bis($\beta$-ethylamine) and a process for preparing said amine.

The diamine itself, 1,4-cyclohexane-bis($\beta$-ethylamine) hereinafter referred to as CBE, is well known to the art and is not claimed to be novel per se. Its use to form polyamides with surprising properties is, however, novel. Processes for preparing amines are well known to the art.

Aromatic alkyl monoamines have been prepared from aromatic nitriles by hydrogenation of the nitrile in the presence of a Raney catalyst such as Raney Nickel or Raney Cobalt; see, for example, U.S. Pat. No. 2,953,490, incorporated herein by reference. Aromatic alkyl amines have been converted to cycloalkyl amines by hydrogenation of the ring in the presence of ruthenium dioxide as the catalyst; see for example U.S. Pat. No. 3,014,966 incorporated herein by reference.

A particularly advantageous method of producing 1,4-cyclohexane-bis ($\beta$-ethylamine) [CBE] is by the reaction of para-xylylene chloride with sodium cyanide to form para-phenylene acetonitrile and thereafter hydrogenating the compound.

The prior art teaches the preparation of para-phenylene acetonitrile from para-xylylene bromide and potassium cyanide using water and ethanol (ca. 1:3 vol. ratio) as the solvent; see for example "Conditions of Formation of Rings Attached to *o, m, p*- positions of the Benzene Nucleus", A. F. Titley, J. Chem. Soc., 1926, 508, which is incorporated herein by reference. Though the prior art method claims a yield of about 70%, this yield is based on the raw product which is a dirty brown in appearance and requires purification by recrystallization. Furthermore, the raw product must be recovered from the reaction system by extraction with ether. Substitution of para-xylylene chloride for the bromide and sodium cyanide for the potassium salt gives essentially the same result.

Surprisingly, however, by judicially selecting the solvent medium, the yield is increased to 85%; but more important, the product is recovered directly by filtration and requires no further purification. Hence, not only is yield increased, but the product is of a higher quality and recovery costs are reduced (i.e. extraction vs. filtration).

It has been found that a particularly advantageous solvent system is dimethyl formamide (DMF) and water. The DMF/H$_2$O volume ratio may vary between about 2:1 to about 1:1.5; preferably, the ratio is between about 2 to 1 to about 1 to 1 more preferably about 1.8 to 1 to about 1.3 to 1.

The reaction is carried out by dissolving the sodium cyanide in the water and slowly adding the para-xylylene chloride dissolved in the DMF to the cyanide solution. There generally is an initial induction period before reaction occurs; thereafter, the reaction is exothermic. It is advantageous to cool the reaction mixture. More preferably, the paraxylylene chloride is added at such a rate that the temperature of the system is maintained at 60°–65°C. It is particularly advantageous to incorporate about 10 to about 25 volume % of the DMF in the water-cyanide solution.

After completion of para-xylylene chloride addition temperature is maintained, by heating, at about 60° to about 65°C. for about 15 minutes to about 1 hour. The product is then precipitated by the addition of about one to about 4 volumes of water based on the total reactant solution volume. Recovery of product, para-phenylene acetonitrile, is by filtration.

The para-phenylene acetonitrile may then be hydrogenated to form 1,4-cyclohexane-bis(β-ethylamine). It is necessary to hydrogenate the nitrile to the amine first in the presence of a Raney catalyst such as Raney Nickel or Raney Cobalt. Preferably, the catalyst is Raney cobalt. Hydrogenation of the aromatic ring is accomplished by using a ruthenium oxide catalyst. The hydrogenation of the nitrile group cannot be affected by this catalyst. Not wishing to be bound by the theory it is thought that the nitrile group either poisons the ruthenium oxide catalyst or deactivates the aromatic ring. Conditions for these hydrogenation reactions and preparation of the catalysts are well known to the art.

In the preparation of the polyamide, the 1,4-cyclohexane bis(β-ethylamine) is reacted with a dicarboxylic acid. The method of preparation is well known to the art. Ordinarily, a salt of the acid is prepared by reacting with the amine, the salt then being heated to drive off water, thereby forming the polyamide. Alternately, it is sometimes advantageous to use a spincrette technique to form fibers of the polyamide by reacting in solution, the amines with the diacid chloride rather than the acid. In this the polyamide is formed, directly, into a fiber suitable for use in the making of synthetic woven fabrics.

Any dicarboxylic acid may be used to form the polyamides of this invention. Carothers et al., have generally disclosed a wide range of dicarboxylic acids suitable for use in the preparation of polyamides; see, for example, U.S. Pat. No. 2,163,584 incorporated herein by reference. These acids may be represented by the general formula:

HOOCCH$_2$RCH$_2$COOH wherein R represents a divalent hydrocarbon radical of at least two methylene groups. For example, R may be alkylene, cycloalkylene, phenylene, xylylene, aralkylene, biphenylene, oxadiphenylene or methylene diphenylene.

Typical of these acids are adipic, pimelic, suberic, sebacic, azelaic, dodecanedioic, 2,2,4-trimethyladipic, 3-methyladipic acids, phenylene diacetic acid, cyclohexane diacetic acid, phenylenedipropionic acid, p,p′-biphenylenediacetic acid, p,p′-oxadiphenylenediacetic acid, p,p′-methylenediphenylene-diacetic acid.

The resulting polymer will typically have the structure:

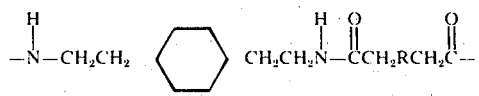

where R is defined as above. Particularly, advantageous fiber forming polyamides are prepared when R is (CH$_2$)$_n$ wherein n is an integer of 2 to 8.

It is obvious to one skilled in the art that mixtures of the aforesaid acids may be used, resulting in the corresponding structures of mixed acids.

Of particular interest is 1,4-cyclohexane diacetic acid. This acid has been found to give surprising and unique results.

Conventional polyamides, i.e. nylon 6,6 and nylon 6, lack high rigidity. This deficiency has prevented their wide use as engineering plastics or for crease-resistant fibers.

It is known that one can synthesize high modulus (high rigidity) polyamides from commercially available diamines by utilizing diacids containing phenylene rings. For example, high modulus polyamides known to the prior art are the condensation products of hexamethylenediamine with terephthalic acid and of hexamethylenediamine with 1,4-phenylene diacetic acid. These polymers, however, are not commercially successful due to their excessively high melting points (360° and 300°C. respectively). Hence, processing is not practical due to decomposition while processing.

Polyamides of a cis-trans mixture of 1,4-cyclohexane dicarboxylic acid give brittle, thermally unstable polyamides. The cause is thought to be due to the deleterious effect of the cis isomer.

Surprisingly, however, superpolyamides of mixtures of cis and trans 1,4-cyclohexane diacetic acid are prepared with advantageous properties such as high modulus, excellent thermal stability and a reasonable melting point from the standpoint of processability.

Any diamine may be used to form these polyamides. As indicated by Carothers, supra, the preferred structure of the diamines is

H$_2$N — CH$_2$R′CH$_2$NH$_2$ wherein R′ is a divalent hydrocarbon radical of at least two carbon atoms. Hence, R′ may be:

(1)  

(2)  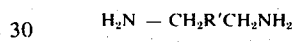 or (3)  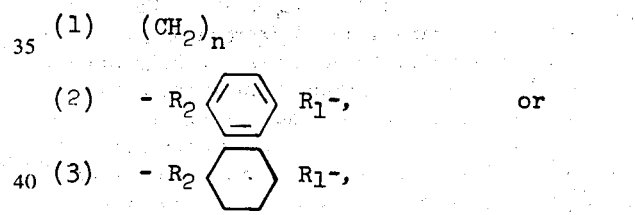

wherein n is a cardinal number from 2 to 18 and R$_1$ and R$_2$ are independently selected from linear or branched chained alkylene radicals. Other suitable diamines are those wherein R′ is p,p′-oxadiphenylene or p,p′-methylenediphenylene.

Alternately, R′ may be a heterogeneous radical wherein R′ is

  (4)

or

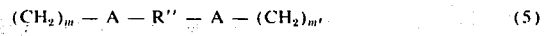  (5)

wherein m and m′ are each cardinal numbers of about 2 to about 5 carbon atoms; and A is selected from the group consisting of oxygen, sulfur and

R″ is C$_2$ to C$_5$ alkylene and R$_3$ is
selected from the group consisting of C$_1$—C$_5$ alkyl, C$_6$—C$_{10}$ aryl or C$_5$—C$_{12}$ cycloalkyl.

Illustrative examples of these diamines are 1,6-hexanediamine, 1,8-octanediamine, 1,10-decanediamine, p-phenylene-bis(β-ethylamine), 1,4-cyclohexane-bis(β-ethylamine), 4-oxa-1,7-heptanediamine, 4-thia-1,7-heptanediamine, 4,7-dioxa-1,10-decanediamine.

The following examples serve to illustrate how this invention may be carried out.

EXAMPLE 1

Seventeen grams of 1,4-cyclohexane-bis($\beta$-ethylamine) of approximately 70% cis, 30% trans isomer composition was dissolved in 100 ml of absolute ethanol. The diamine was reacted with 14 grams of adipic acid dissolved in 250 ml of absolute ethanol. The precipitated white salt was filtered and air dried.

Five grams of the above salt was placed in a heavy walled tube which was evacuated, sealed and heated to

TABLE I

EFFECT OF INCREASING DIAMINE MOLECULE LENGTH ON MELTING POINT OF POLYAMIDES

| Diamine | Melting Point of Polyamide °C. | | |
|---|---|---|---|
| | Adipic | Suberic | Sebacic |
| $H_2N-(CH_2)_6-NH_2$ | 260–263 | 215–220 | 209 |
| $H_2N-(CH_2)_8-NH_2$ | 235 | 200–205 | 197 |
| $H_2N-C-\bigcirc-C-NH_2$ (70% cis, 30% trans) | 258 | 237 | 205 |
| $H_2N-C-C-\bigcirc-C-C-NH_2$ (70% cis, 30% trans) Predicted | 230 | 220 | 195–200 |
| Actual | 273 | 244 | 237 |

215°C. for 2 hours. The tube was then opened and heated for about ½ hour at 285°C. under nitrogen at atmospheric pressure and for about one-half hour at a reduced pressure of 10 to 6 mm Hg.

The resulting product was an opaque polyamide having a crystalline melting point of 257°–273°C. and an inherent viscosity of 2.0 (measured at 25°C. from a 0.5% solution of polymer in m-cresol).

EXAMPLE 2

A salt was prepared as in Example 1 using about 5 grams of CBE (55% cis 45% trans) in 50 ml ethanol and 4.1 grams of adipic acid in 150 ml ethanol. The air dried salt was reacted in a sealed tube at 220°C. for 2½ hours; then under nitrogen at atmospheric pressure for 1½ hours at 300°C and finally for ¼ hour at 2–6 mm Hg pressure at 300°C. The resulting polyamide had a melting point of 265°–302°C.

EXAMPLE 3

A solution of 5 g. 1,4-cyclohexane-bis($\beta$-ethylamine), composed of 93% cis, 7% trans isomers, in 50 ml of absolute ethanol was mixed with a solution of 4.1 g. adipic acid in 150 ml of ethanol. The resulting salt was dried and heated as in Example 2, except that the final temperature cycle was 280°C. The polyamide formed had a melting point of 188°–214°C.

Examples of 1–3 show that increasing the percentage of cis isomer results in a lowering in melting point. This is consistent with the prior art teachings of U.S. Pat. No. 3,012,994 incorporated herein by reference. It will be noted, however, that the patent, relating to cyclohexane-bis(methylamine) [CBM] polyamides, shows substantially lower melting points for similar products. For example, a 30% cis, 70% trans mixture of CBM reacted with adipic acid melts at 295°–303°C. (equivalent to 55 cis 45 trans CBE) whereas a 50% cis, 50% trans mixture results in an adipic polyamide which melts at 265°–273°C. (equivalent to 70% cis, 30% trans mixture of Example 1). By contrast, a 75% cis, 25% trans mixture results in a polyamide which melts at 185°–192°C., a melting point below that obtained with a 93% cis, 7% trans CBE/adipic acid polyamide (Example 3). Hence, it is demonstrated that equivalent polyamides formed from CBE melt at a higher melting point than CBM polymers.

To further illustrate the fact that CBE polymers have a higher melting point and that this is contra to what would be predicted, Table I shows various polyamides of increasing amine chain length compared with CBE and CBM polyamides.

The comparative data show that CBE polyamides have melting points between 25°–40°C. higher than their predicted values and at least 10°C. higher than the equivalent CBM polymer. The predicted data are based on the effect of increasing the diamine chain length by two methylene groups.

EXAMPLE 4

Polyamides were prepared in the manner of Example 1 using suberic and sebacic acids in place of adipic acid. The CBE-suberic acid polyamide had a melting point of 244°C. and an inherent viscosity of 1.5. The CBE-sebacic acid polyamide melted at 237°C. and had an inherent viscosity of 1.17.

EXAMPLE 5

A polyamide salt was prepared from 5.00 g. of 1,4-cyclohexane diacetic acid (68% cis, 32% trans) and 4.42 g. of 1,4-cyclohexane-bis ($\beta$-ethylamine) (70% cis, 30% trans). Five grams of the salt was polymerized in the manner of Example 1 first by heating to 230°C. for one hour, then at 280°C. for ½ hour under nitrogen and ¾ hour at 4 mm Hg pressure. The final polyamide was tough and clear with a melt temperature of 210°–220°C.

EXAMPLE 6

A solution of 130 grams (2.65 moles) sodium cyanide in 200 ml of water was placed in a four-necked flask, equipped with a thermowell, mechanical stirrer, electrically heated addition funnel and a condenser. A solution of 200 grams (1.15 mole) of p-xylylene chloride in 200 ml of dimethyl formamide was added dropwise with constant stirring and such a rate as to maintain the reaction temperature at 60°–65°C. The p-xylylene chloride solution was maintained at about 60°C. to prevent solid precipitation. The reaction was exothermic and addition took 2 hours. At the completion of the addition, the temperature was maintained by external heating for an additional hour. The mixture was then poured into 2 liters of water. The precipitated solid was filtered and washed with an additional liter of water. The product yield was 85% (ca. 152 g.) of paraphenylene diacetonitrile having a melting point of about 95°–97°C.

| Property | CBE-6 Polyamide | 6,6 Polyamide |
|---|---|---|
| M.P. °C. | 257–273° | 255–260° |
| Moisture Regain | | |
| (a) Saturated | 6.7 | 7.1 |
| (b) 70°F./65% Humid. | 3.4 | 4.5 |
| Tensile (psi.) | | |
| At Yield | 8–10,900 | 9–11,000 |
| At Break | 9,500 | 7,500 |
| Elongation, % | 455 | 300 |
| Flex. Modulus | | |
| (psi. at 73°F.) | 430,000 | 240,000 |
| Density | 1.09 | 1.13 |
| Degradation Temperature | | |
| (°C., under $N_2$) | 368 | 370 |

CBE-6 polyamide shows obvious advantages over nylons 6,6 and 6 in having lower moisture regain, higher tensile strength, much higher flexural modulus and lower density.

EXAMPLE 7

6-CDA (70% cis, 30% trans) polyamide

A solution of 10 grams (0.05 mole) 1,4-cyclohexane diacetic acid (CDA) in 200 ml of absolute ethanol was mixed with constant stirring with 6.0 grams (0.052 mole) hexamethylene diamine dissolved in 50 ml of ethanol. The precipitated nylon salt was allowed to stand overnight and then was filtered and air dried. The pH of 1% aqueous solution of this salt was 7.9. 5 g. of the nylon salt was placed in a heavy wall tube which was evacuated, sealed and heated at 218°–220°C. for 2.5 hours. After the tube was cooled it was opened and the polymerization continued at 280°C. for 50 minutes under nitrogen and for 40 minutes at 0.5 mm Hg. Throughout the under vacuum polymerization, nitrogen was bubbled into the molten polymer via a capillary. Melting point of the resultant polyamide 221°–247°C. (DTA). $\eta_{inh} = 1.34$.

EXAMPLE 8

8-CDA (70% cis, 30% trans) polyamide

A polyamide salt was prepared as described in the previous example from 5.00 g. (0.035 mole) 1,8-octanediamine and 6.61 g. (0.033 mole) 1,4-cyclohexane diacetic acid. 5 g. of this salt was placed in a heavy wall tube which was evacuated, sealed and heated at 220°–225°C. for 2.5 hours. The polymerization tube was opened, a capillary, connected with a nitrogen source, was introduced and the tube was heated for 1.5 hours under nitrogen and for 1.25 hours under vacuum. Polyamide m.p. 209°C. $\eta_{inh} = 1.40$.

EXAMPLE 9

10-CDA (70% cis, 30% trans) polyamide

A polyamide salt was prepared as in Example 7 from 5.00 g. (0.029 mole) 1,10-decanediamine and 5.70 g. (0.028 mole) 1,4-cyclohexane diacetic acid. 5 g. of this salt was heated in an evacuated and sealed thick wall tube for 2.5 hours at 220°–225°C. The prepolymer thus prepared was further heated at 280°C. for 1.5 hours under nitrogen and 1.25 hours under vacuum. Softening point of the noncrystalline polyamide, 210°C. $\eta_{inh} = 1.54$.

EXAMPLE 10

5-CDA (70% cis, 30% trans) polyamide

A polyamide salt was prepared by mixing a solution of 8.40 g. (0.042 mole) 1,4-cyclohexane diacetic acid in 150 ml absolute ethanol with a solution of 4.5 g. (0.044 mole) 1,5-pentanediamine in 100 ml ethanol. The nylon salt which precipitated out was filtered and air dried to constant weight. 5 g. of this salt was placed in a heavy wall tube sealed and heated for 2.5 hours at 220°C. The resultant prepolymer was further heated at 280°C. for 1.5 hours under nitrogen and for 1 hour under vacuum. $\eta_{inh} = 1.46$. Softening Point 140°C.

EXAMPLE 11 m-Xylylenediamine-CDA (70% cis, 30% trans) Polyamide m-Xylylenediamine 5.0 g. (0.037 mole) and 7.0 g. (0.035 mole) of 1,4-cyclohexane diacetic acid were used to prepare a nylon salt in the manner described in previous examples. 5 g. of this salt was heated in an evacuated heavy wall tube at 220°C. for 2.5 hours. The prepolymer was further heated at 300°C. for 1.5 hours under nitrogen and for 1 hour under vacuum. m.p. 271°–282°C. $\eta_{inh} = 0.47$.

Examples 7–11 demonstrate that suitable polyamides having melting points within the processing range of these polymers may be prepared.

In order to show the unique advantage of 1,4-cyclohexane diacetic acid polyamides, a comparison of the physical properties of 6-CDA polyamide (Example 1) nylon 6 and nylon 6,6 is presented in Table II.

TABLE II

Comparison of Conventional 6 and 6,6 Polyamides with 1,4-Cyclohexane Diacetic Acid Polyamide

| Property | 6-CDA Polyamide | 6 Polyamide | 6,6 Polyamide |
|---|---|---|---|
| M.P. °C. | 220–244° | 210–215° | 255–260° |
| % Moisture regain (saturated) | 6.9 | 9.5 | 7.1 |
| Tensile strength (psi) | | | |
| a) At yield | 13,190 | 8,700 | 9–11,000 |
| b) At break | 9,440 | — | 7,500 |
| Elongation % | 178 | 285 | 300 |
| Flex. Modulus (psi. at 73°F.) | 475,000 | 108,000 | 240,000 |
| Density | 1.10 | 1.13 | 1.13 |

These data demonstrate that comparable polyamides when prepared with 1,4-cyclohexane diacetic acid have higher rigidity (modulus), greater tensile strength and lower moisture regain. Furthermore, these properties are achieved in a polymer having a melting point similar to those polyamides (nylon 6 and nylon 6,6) commercially in use.

Since it will be readily evident to one skilled in the art that many different embodiments may be made without departing from the spirit of this invention, it is not intended to limit the scope thereof to the particular embodiments disclosed herein.

EXAMPLE 12

Polyamides have been prepared from 1,2-cyclohexane-bis(ethylamine); see for example German Pat. No. 924240. As a comparison to the polyamides of this invention an adipic acid polyamide of 1,2-cyclohexane-bis(ethylamine) follows:

1,2-cyclohexane-bis(ethylamine) (17.6 m moles) and 17.2 m moles of adipic acid were sealed in an evacuated polymerization tube. The reaction mixture was gradually heated to 200°C. using an aluminum block heater. The temperature was maintained for 2 hours. After cooling to room temperature the tube was opened and a capillary connected to a nitrogen line inserted. The reaction mixture was heated to 270° under a slow stream of nitrogen for 1½ hours. This was followed by evacuation of the tube while nitrogen was bubbled into the polymer mass and heating was continued for 1½ hours.

The recovered polymer had an inherent viscosity of 0.82, a softening point of 95°C. and a melting point of 105°C. Melting point as determined by DTA was 75°C. By way of comparison the 1-4 diamine of this invention, when reacted with adipic acid, formed a polyamide having a melting point of 273°C. Hence the position of the ethylamine groups on the cyclohexane ring is critical.

EXAMPLE 13

The crystallinity of polyamides of this invention and 1,4-cyclohexane-bis(methylamine) adipic acid condensation polymer were determined by differential thermal analysis (DTA). FIG. 1A is the DTA curve for the 1,4-cyclohexane-bis(methylamine) adipic acid reaction product while FIG. 1B is the similar curve for the 1,4-cyclohexane-bis(ethylamine) adipic acid reaction product of this invention. The area beneath the broken line and the curve is, in each case, a measure of crystallinity; the larger the area, the greater the crystallinity. It is readily evident that the bis(methylamine) product is low in crystallinity while the bis(ethylamine) product of this invention is high in crystallinity.

What is claimed is:

1. A fiber forming polyamide consisting essentially of the repeating unit:

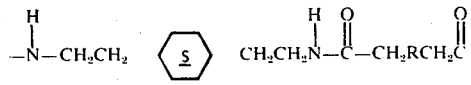

wherein R is an alkylene, cyclohexylene, or mixtures thereof.

2. The polyamide of claim 1 wherein the alkylene radical is a divalent group of the general formula:

$$-(CH_2)_n-$$

wherein $n$ is an integer of about 2 to about 8.

3. The polymer of claim 1 wherein the

radical is derived from an acid selected from the group consisting of adipic, suberic, sebacic, azelaic or 1,4-cyclohexane diacetic acid.

4. A fiber forming polycarbonamide consisting of the polymeric condensation product of an alkylene dicarboxylic acid and 1,4-cyclohexane bis(ethylamine).

* * * * *